United States Patent [19]

Ljungdahl et al.

[11] 4,292,407

[45] Sep. 29, 1981

[54] ANAEROBIC THERMOPHILIC CULTURE

[75] Inventors: Lars G. Ljungdahl, Athens, Ga.; Jürgen K. W. Wiegel, Göttingen, Fed. Rep. of Germany

[73] Assignee: The United States of America as represented by the United States Department of Energy, Washington, D.C.

[21] Appl. No.: 74,287

[22] Filed: Sep. 11, 1979

[51] Int. Cl.³ .............................................. C12P 7/06
[52] U.S. Cl. ..................................... 435/161; 435/801
[58] Field of Search ............... 435/161, 162, 801, 842, 435/172

[56] References Cited

U.S. PATENT DOCUMENTS 4,094,742  6/1978  Bellamy .......................... 435/165 X

OTHER PUBLICATIONS

Smith et al., Bergeys Manual of Determinative Bacteriology, Eight Ed., Williams & Wilkins Co., Publishers (1974), pp. 551–572.

McBee, "The Characteristics of Clostridium Thermocellum", J of Bacteriology, vol. 67 (1954), pp. 505–506.

Primary Examiner—R. B. Penland
Attorney, Agent, or Firm—Allen F. Westerdahl; Raphael V. Lupo; James E. Denny

[57] ABSTRACT

A newly discovered thermophilic anaerobe is described that was isolated in a biologically pure culture and designated *Thermoanaerobacter ethanolicus* ATCC 3/550. *T. Ethanolicus* is cultured in aqueous nutrient medium under anaerobic, thermophilic conditions and is used in a novel process for producing ethanol by subjecting carbohydrates, particularly the saccharides, to fermentation action of the new microorganism in a biologically pure culture.

11 Claims, No Drawings

ANAEROBIC THERMOPHILIC CULTURE

This invention is the result of a contract with the U.S. Department of Energy.

BACKGROUND OF THE INVENTION

This invention relates to biologically pure cultures of microorganisms and, more particularly to strains of a newly discovered thermophilic ethanol forming anaerobe. Further, the invention relates to the preparation of pure cultures of said anaerobe and to a novel process for producing ethanol therefrom.

Relatively few anaerobic microorganisms have been isolated and characterized that grow on carbohydrates (are glycolytic) and yield ethanol under thermophilic and extreme thermophilic conditions. Representative examples of well-characterized glycolytic anaerobic bacteria that will grow in a nutrient culture in the thermophilic to extreme thermophilic ranges belong to the genus Clostridium and include: *C. Thermoaceticum, C. tartarivorum, C. thermosaccharolyticum, C. thermocellum, C. thermocellulaseum* and *C. thermohydrosulfuricum*. Strains of the latter have been isolated and characterized by J. Wiegel and L. G. Ljungdahl (See Abstract I 75 of the Abstract of the Annual Meeting of the American Society of Microbiology, Las Vegas, Nev., U.S.A., 1978). A neotype strain of *C. thermohydrosulfuricum* E 100-69 was isolated from the liquors of an Austrian sugar beet factory by F. Hollaus and U. Sleytr (See Arch. Mikrobiol. 86: 129-146, 1972).

These microorganisms are, of course, of interest for the possible anaerobic fermentation of various carbohydrates, such as saccharides, to assist in combination (mixed cultures) with other bacteria to efficiently break down cellulose, and for the direct production of ethanol and other products of fermentation under thermophilic conditions. Yeast (Saccharomyces species) fermentation of sugar, as is well known, ordinarily must be conducted at less than about 37° C. under semiaerobic conditions to yield ethanol. Further, the conditions must be carefully controlled to avoid contamination of harmful bacteria, fungi, and molds.

In the isolation of thermophilic anaerobic bacteria, in particular, *Clostridium* species, from mud samples from the hot springs at various locations in Yellowstone National Park, U.S.A., two strains of a new anaerobic thermophilic glycolytic species have been discovered. In the isolation, purification and characterization of this newly discovered species, which is not a Clostridium, it has been found that the new species is an efficient producer of ethanol from various carbohydrates, in particular, the most common mono- and di-saccharides. As is disclosed and claimed in a copending application, Ser. No. 074,086, filed on the same date by the same inventors, the newly discovered species disclosed herein is also useful in mixed nutrient cultures (i.e., with certain *Clostridia* species) for the production of ethanol from cellulose.

SUMMARY OF THE INVENTION

Accordingly, it is an object of the present invention to provide biologically pure cultures of a newly discovered anaerobic thermophilic species. It is also an object of the invention to provide a process for producing ethanol using biologically pure cultures of said newly discovered anaerobe.

The newly discovered thermophilic anaerobe is a new species of a new genus isolated in a biologically pure culture and designated herein as *Thermoanaerobacter ethanolicus*. A representative strain of this new microorganism in a biologically pure subculture, designated JW 200, has been deposited in the patent strain collection of the American Type Culture Collection, Rockville, Md., U.S.A. ATCC 31550 is the accession number assigned by the American Type Culture Collection to this strain.

The isolated strain of *T. ethanolicus* has been cultured in aqueous nutrient medium under anaerobic, thermophilic conditions to produce a recoverable quantity of ethanol. Accordingly, the novel process of the present invention is a process for producing ethanol which comprises subjecting certain carbohydrates to fermentation action of the newly isolated microorganism *T. ethanolicus* in a biologically pure culture to form ethanol and recovering said ethanol.

For the purposes of this specification, the term "thermophilic" refers to a culture temperature between about 45° C. to 70° C. and the term "extreme thermophilic" refers to culture temperatures between about 70° to 80° C.

As will be apparent to those skilled in the art from the following description and examples and from the unique morphology and fermentation pattern, in particularly the ability of the microorganism to grow at thermophilic and extreme thermophilic temperature, the newly-discovered *T. ethanolicus* is clearly distinguishable from other anaerobic thermophilic genera.

DETAILED DESCRIPTION OF THE PREFERRED EMBODIMENT

The microorganism of the present invention was discovered in and isolated from mud samples of hot springs in Yellowstone National Park, Wyoming, U.S.A. One strain JW-201 was isolated from an acidic spring, the Dragon Mouth, with a pH of about 5.5 and the second strain JW 200 from a alkaline spring, White Creek, with a pH of about 8.8. The strains are very similar and were discovered in association with the anaerobic thermophilic *Clostridia* strains hereinabove mentioned.

Although the new microorganism strains share the ability to ferment certain carbohydrates at thermophilic temperatures with the *Clostridia* mentioned above, they do not form spores and are therefore excluded from the genus *Clostridium*. Other characteristics exclude them from characterized and known genera. In view of the morphology and fermentation characteristic, hereinafter described, these new strains are deemed a new genus and species designated *Thermoanaerobacter ethanolicus*, ATCC 31550 being representative of these strains.

Isolation of the new strains from the mud samples was accomplished using the anaerobic technique according to Hungate, (Bacteriol. Rev. 14: 1-49) as modified by Bryant and Robinson, (J. Dairy Science 44; 1446-1456), which technique will be familiar to those skilled in the art. The medium use for isolation and enrichment cultures and to maintain the isolated strains has the following preferred composition: $KH_2PO_4$, 1.5 g/l; $Na_2HPO_4.12H_2O$, 4.2 g/l; $NH_4Cl$, 0.5 g/l; $MgCl_2$, 0.18 g/l; yeast extract (Difco), 2.0 g/l; glucose, 8.0 g/l; and Wolfe's mineral solution, 5 ml. The medium is prepared under anaerobic conditions and must be stored under an atmosphere of an inert gas, such as nitrogen or argon. The pH of the medium is in the range of about 6.8 and 7.8, preferably 7.3, and is adjusted as required with a sterile, anaerobic NaOH or HCl solution. Stock cultures are maintained on the same medium solidified with 2% agar and stored at 4° C. Liquid medium cultures can be stored at −18° C. after the addition of an equal volume of glycerol.

Although in the exemplary nutrient medium, glucose is the preferred carbohydrate substrate, other monosaccharides, such as, xylose, ribose, mannose, fructose and galactose, and disaccharides, such as sucrose, lactose, maltose and cellobiose can be used. Growth also occurs on pyruvate, pectin, and starch. It should be noted that both strains of T. ethanolicus require yeast extract for growth. Without yeast extract, no growth was obtained in subsequent subcultures. Although growth is much less than in the presence of glucose, yeast extract concentrations above 0.5% can serve as the only carbon, nitrogen and energy source.

The new strains of Thermoanaerobacter ethanolicus ATCC 31550 (JW 200) can be conveniently cultured using the same nutrient medium as used for isolation under anaerobic conditions at temperatures between about 36° C. and 78° C. with the optimum temperature for growth being about 68° C. Doubling time at 68° C. is about 90 minutes. It is significant, however, that excellent growth can be also maintained at higher temperature, such as 72° C., doubling time at this temperature being about 120 minutes. The ability to maintain a significant growth at these extreme thermophilic conditions is, of course, one of the distinguishing characteristics of T. ethanolicus. Such growth is not pH dependent in that growth occurs in the very wide pH range of from 4.5 to 9.8. For optimum growth, the pH of the medium should be between about 5.7 and 8.6, with the preferred pH being about 7.3.

Another distinguishing characteristic of T. ethanolicus in its ability under the above described conditions to ferment a wide variety of saccharides with a significant yield of ethanol. As will be shown in specific examples, hereinafter, a yield of ethanol as high as 1.8 mole of ethanol per mole of fermented glucose has been achieved at a temperature of 60° C. and at a pH of 7.8 under anaerobic conditions. However, to maintain a process of ethanol fermentation, when concentrations of ethanol reach about 5%, the ethanol should be removed by conventional distillation techniques. Such a distillation can be accomplished using reduced pressure (partial vacuum) even during fermentation in the presence of the microorganism T. ethanolicus since the organism will tolerate the boiling point of ethanol (78° C.). Of course, growth will be slower at higher than preferred temperatures.

The following specific examples serve to further illustrate the present invention in its preferred embodiments.

EXAMPLE I

Isolation of Thermoanaerobacter ethanolicus

Samples from the hot springs of Yellowstone National Park were collected under sterile anaerobic conditions. One g of samples were used to incubate 100 ml of the nutrient medium described hereinabove. The samples were incubated at 74° C. After 3 days dilution rolls were made using anaerobic tubes in accordance with the Hungate technique as modified by Bryant and Robinson. After 2 days incubation at 74° C., agar shakes were made from the tubes of the highest dilution which exhibited growth. The nutrient medium, supplemented with 2% agar was used for the agar cultures. The agar shakes were rolled out and incubated at 60° C. in a 30° slanted position. Final strain cultures were obtained by selecting single colonies and repeating the agar shake procedure several times.

Two strains of a new genus and new species were discovered and isolated in biologically pure form using this technique and designated JW 200 and JW 201, respectively. The two strains are very similar.

These newly discovered strains were analyzed using conventional microbiologically techniques which resulted in characterization and identification as follows:

a. Morphology: Cells grown at 60° C. show tumbling motility. Older cells, or grown in liquid or at higher temperatures, such as 75° C. show less motility although they are flagellated. The flagellation is of the retarded peritrichous type, with between 1 and 10 flagella that are up to 80 $\mu$m long. Young cell rods during logarithmic growth often show pointed ends. These rods are 4 to 8 $\mu$m long and 0.6 to 0.9 $\mu$m thick. Cell rods of the late logarithmic growth phase can grow up 200 $\mu$m long, which then may divide into chains of bacteria during the beginning of the stationary growth phase.

b. Spores: Spores are not formed.

c. Other Characteristics: The strains are strictly anaerobic, gram-variable, catalase-negative, pyruvate is metabolized via pyruvate-ferredoxin reductase system. Two anaerobic ferredoxins and a rubredoxin are present.

d. Growth requirements: Yeast extract (0.2%) and a carbon source is required. Ammonium ions are not required as a nitrogen source.

e. Substrate: Glucose, other monosaccharides, and disaccharides can be used. Growth also occurs on pyruvate, pectin, starch and to a small extent on yeast extract. Cellulose is not degraded. The yields of ethanol from diverse carbohydrate substrates are shown in Example 5 and Table III, below.

f. Fermentation Products: The strains ferment glucose to ethanol and $CO_2$ as the main fermentation products and acetate, lactate and $H_2$ as minor products. It has been determined that glucose ferments to ethanol mainly on the Embden-Mayerhof pathway.

g. pH Range: 4.5–9.8. Optimum pH range: 5.7–8.6.

h. Temperature Range:
  Temperature minimum=36° C. ($T_d$ at 37° C.=>100 hours)
  Temperature optimum=68° C. ($T_d$ at 68° C.=1.5 hours)
  Temperature maximum=78° C. ($T_d$ at 76° C.=approximately 10 hours) ($T_d$=doubling or generation time)

i. Guanosine plus Cytosine (G+C) content of deoxyribonucleic acid (DNA): About 38% as determined with a buoyant density method and 32% as determined using a thermal denaturation method.

j. Taxonomy: The newly isolated strains JW 200 and JW 201 have some characteristics similar to Clostridium thermohydrosulfuricum, the only other known extreme thermophilic, anaerobic, glycolytic bacteria. However, the new strains do not form spores, thus excluding them from the genus Clostridium. Other properties described in this application appear to exclude the new strains from previously identified genera that are described in the 8th edition of Bergey's Manual of Determinative Bacteriology (Williams and Wilkins Comp. Baltimore) 1974. Therefore, the new strains represent a new genus and new species that has been named *Thermoanaerobacter ethanolicus* ATCC 31550 is representative of these strains.

EXAMPLE 2

Fermentation Using *T. ethanolicus*

Glucose was fermented by *T. ethanolicus* ATCC 31550 in culture tubes containing 5 ml of medium using conventional techniques at 72° C. under an argon atmosphere and with a starting pH of 7.5. 44 µmoles/ml of glucose was fermented to yield the following products: ethanol 78.4 µmoles/ml; acetate 4.5 µmoles/ml; lactate 4.0 µmoles/ml; $CO_2$ 89.2 µmoles/ml; and $H_2$ 4.3 µmoles/ml. This example shows a complete fermentation balance with an ethanol yield of 1.76 moles of ethanol per mole of glucose.

EXAMPLE 3

Fermentation at Different Temperatures

Three samples of glucose were fermented under conditions given in Example 2 except for different temperatures by *T. ethanolicus* ATCC 31550 at a starting pH of 7.8 under an argon atmosphere. The results are shown in the following table.

TABLE I

| | Temperature | | |
|---|---|---|---|
| | 55° C. | 60° C. | 72° C. |
| Substrate: | µmoles/ml | µmoles/ml | µmoles/ml |
| Glucose | 24.2 | 26.1 | 23.0 |
| Products: | | | |
| Ethanol | 40.0 | 48.0 | 38.0 |
| Acetate | 5.5 | 3.2 | 4.0 |
| Isobutyrate | 0.05 | 0.05 | 0.08 |
| Isovalerate | 0.075 | 0.05 | 0.08 |
| Lactate | 2.2 | 2.1 | 2.6 |
| $CO_2$ | (not determined) | | |
| Ethanol Yield in moles/ mole glucose | 1.65 | 1.83 | 1.65 |

EXAMPLE 4

Fermentation Reproducibility

Three fermentations of glucose using *T. ethanolicus* ATCC 31550 were conducted at 72° C. and pH 7.2 under an argon atmosphere. Other conditions were those given in Example 2. Each fermentation contained 45 µmoles/ml of glucose. The results are shown in the following Table II.

TABLE II

| | FERMENTATION | | |
|---|---|---|---|
| | 1 | 2 | 3 |
| Products | µmoles/ml | µmoles/ml | µmoles/ml |
| Ethanol | 78.3 | 77.5 | 80.0 |
| Acetate | 6.5 | 5.2 | 4.2 |
| Lactate | 3.5 | 7.2 | 4.9 |
| Ethanol Yield in moles/mole glucose | 1.74 | 1.72 | 1.77 |

EXAMPLE 5

Fermentation Using Diverse Substrate

Diverse sources of carbohydrate substrate were fermented by *T. ethanolicus* ATCC 31550. The fermentations were for 48 hours in 10 ml cultures containing 50 mg of the carbohydrate substrate at a temperature of 68° C. and at pH 6.8 under a nitrogen atmosphere. The results are shown in the following Table III.

TABLE III

| Carbohydrate Substrate | Ethanol Yield mg |
|---|---|
| Galactose | 17.7 |
| Mannose | 13.4 |
| Lactose | 16.2 |
| Maltose | 18.4 |
| Cellobiose | 12.4 |
| Sucrose | 15.9 |
| D-ribose | 13.0 |
| D-xylose | 15.2 |
| Pyruvic acid | 11.1 |
| Starch, potatoe | 13.8 |
| Starch, corn, soluble | 18.8 |
| Starch, corn, insoluble | 16.1 |
| Pectin | 16.6 |

What is claimed is:

1. A biologically pure culture of the microorganism *Thermoanaerobacter ethanolicus*, having the identifying characteristics of ATCC 31550, said culture having the ability to product ethanol upon fermentation in an aqueous nutrient medium containing a substrate selected from the group consisting essentially of the monosaccharides, disaccharides, pyruvate, pectin, and starch.

2. The biologically pure culture of claim 1, wherein said substrate is selected from the group consisting essentially of glucose, fructose, D-ribose, xylose, D-mannose, D-galactose, sucrose, cellobiose, lactose, maltose, pyruvate, pectin, and starch.

3. The thermophilic ethanol-forming anaerobe *Thermoanaerobacter ethanolicus*, having the identifying characteristics of ATCC 31550, in a biologically pure culture, said culture having the ability to yield ethanol as a major product constituent upon fermentation under anaerobic, thermophilic conditions in an aqueous nutrient medium containing a substrate selected from the group consisting essentially of the monosaccharides, disaccharides, pyruvate, pectin, and starch.

4. The biologically pure culture of claim 3, wherein said fermentation is under extreme thermophilic conditions.

5. A process which comprises cultivating *Thermoanaerobacter ethanolicus*, having the identifying characteristics of ATCC 31550, in an aqueous nutrient medium containing a substrate selected from the group consisting essentially of the monosaccharides, disaccharides, pyruvate, pectin, and starch under anaerobic, thermophilic conditions until a recoverable quantity of ethanol is produced.

6. The process of claim 5, wherein said process is conducted under extreme thermophilic conditions.

7. A process for producing ethanol which comprises subjecting an aqueous nutrient medium containing a substrate selected from the group consisting essentially of the monosaccharides, disaccharides, pyruvate, pectin, and starch to the fermentation action of the microorganism *Thermoanaerobacter ethanolicus*, having the identifying characteristics of ATCC 31550, to form ethanol and recovering said ethanol.

8. The process of claim 7, wherein said fermentation is conducted under anaerobic, thermophilic conditions.

9. The process of claim 7, wherein said fermentation is conducted under anaerobic, extreme thermophilic conditions.

10. The process of claim 7, wherein said fermentation is conducted under anaerobic conditions at a pH range of about 5.7 to 8.6.

11. The process of claim 7, wherein the fermentation is conducted under anaerobic conditions at temperatures between about 36° C. to 80° C.

* * * * *